US00PP17999P2

(12) United States Plant Patent
Schräder

(10) Patent No.: US PP17,999 P2
(45) Date of Patent: Sep. 11, 2007

(54) *VERBENA* PLANT NAMED 'SUMVERDI 01'

(50) Latin Name: *Verbena hybrida*
Varietal Denomination: Sumverdi 01

(76) Inventor: Ralf Schräder, Karl-Leisner-Str. 15, 59348 Lüdinghausen (DE)

( * ) Notice: Subject to any disclaimer, the term of this patent is extended or adjusted under 35 U.S.C. 154(b) by 0 days.

(21) Appl. No.: 11/323,157

(22) Filed: Dec. 30, 2005

(51) Int. Cl.
*A01H 5/00* (2006.01)

(52) U.S. Cl. ..... Plt./308
(58) Field of Classification Search ..... Plt./308
See application file for complete search history.

(56) References Cited

PUBLICATIONS

GTITM UPOVROM Citation for 'Sumverdi 01' as per QZ PBR 20041069; Jun. 14, 2004.*

* cited by examiner

*Primary Examiner*—Kent Bell
(74) *Attorney, Agent, or Firm*—C. A. Whealy

(57) ABSTRACT

A new and distinct cultivar of *Verbena* plant named 'Sumverdi 01', characterized by its compact, upright and mounded plant habit; early and freely flowering habit; light violet-colored flowers; and good garden performance.

1 Drawing Sheet

Botanical designation: *Verbena hybrida.*
Cultivar denomination: 'SUMVERDI 01'.

BACKGROUND OF THE INVENTION

The present Invention relates to a new and distinct cultivar of *Verbena* plant, botanically known as *Verbena hybrida,* and hereinafter referred to by the name 'Sumverdi 01'.

The new *Verbena* is a product of a planned breeding program conducted by the Inventor in Lüdinghausen, Germany. The objective of the breeding program is to develop new early flowering *Verbena* cultivars with a mounded plant habit.

The new *Verbena* originated from a cross-pollination made by the Inventor in March, 2002 of a proprietary seedling selection of *Verbena hybrida* identified as Seedling 10, not patented, as the female, or seed, parent with a proprietary seedling selection of *Verbena hybrida* identified as Seedling 1–5, not patented, as the male, or pollen, parent. The cultivar Sumverdi 01 was discovered and selected by the Inventor as a flowering plant within the progeny from the aforementioned cross-pollination in a controlled environment in Lüdinghausen, Germany in September, 2002.

Asexual reproduction of the new cultivar by cuttings at Lüdinghausen, Germany, since October, 2002, has shown that the unique features of this new *Verbena* are stable and reproduced true to type in successive generations of asexual reproduction.

SUMMARY OF THE INVENTION

The following traits have been repeatedly observed and are determined to be the unique characteristics of 'Sumverdi 01'. These characteristics in combination distinguish 'Sumverdi 01' as a new and distinct cultivar:

1. Compact, upright and mounded plant habit.
2. Early and freely flowering habit.
3. Light violet-colored flowers.
4. Good garden performance.

Plants of the new *Verbena* differ from plants of the female parent selection in the following characteristics:

1. Plants of the new *Verbena* flower earlier than plants of the female parent selection.
2. Plants of the new *Verbena* have larger flowers than plants of the female parent selection.
3. Flowers of plants of the new *Verbena* are darker in color than flowers of plants of the female parent selection.

Plants of the new *Verbena* differ primarily from plants of the male parent selection in plant size as plants of the new *Verbena* are more compact than plants of the male parent selection.

The new *Verbena* can be compared to the cultivar, Sumverb 02, disclosed in U.S. Plant Pat. No. 14,584. However, in side-by-side comparisons conducted in Lüdinghausen, Germany, plants of the new *Verbena* differed from plants of the cultivar Sumverb 02 in the following characteristics:

1. Plants of the new *Verbena* were more compact and had shorter internodes than plants of the cultivar Sumverb 02.
2. Plants of the new *Verbena* were more freely branching than plants of the cultivar Sumverb 02.
3. Plants of the new *Verbena* had smaller leaves than plants of the cultivar Sumverb 02.
4. Plants of the new *Verbena* flowered earlier than plants of the cultivar Sumverb 02.
5. Plants of the new *Verbena* were more freely flowering than plants of the cultivar Sumverb 02.
6. Plants of the new *Verbena* had smaller inflorescences and smaller flowers than plants of the cultivar Sumverb 02.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Verbena*. The photograph comprises a side perspective view of a typical plant of 'Sumverdi 01' grown in a container.

DETAILED BOTANICAL DESCRIPTION

In the following description, color references are made to The Royal Horticultural Society Colour Chart, 2001 Edition, except where general terms of ordinary dictionary significance are used. Plants grown in 10.5-cm containers were used for the aforementioned photograph and following description. Plants has been growing for about two months when the photograph and the description were taken. Plants were grown under conditions which closely approximate commercial production conditions during the summer in Lüdinghausen, Germany in an outdoor nursery. During the production period, day temperatures ranged from about 16° C. to about 30° C. and night temperatures ranged from about 8° C. to about 14° C.

Botanical classification: *Verbena hybrida* cultivar Sumverdi 01.

Parentage:

*Female parent.*—Proprietary seedling selection of *Verbena hybrida* identified as Seedling 10, not patented.

*Male parent.*—Proprietary seedling selection of *Verbena hybrida* identified as Seedling 1–5, not patented.

Propagation:

*Type cutting.*—Vegetative tip cuttings.

*Time to initiate roots, summer.*—About 14 days at 16° C.

*Time to initiate roots, winter.*—About 18 days at 16° C.

*Time to develop roots, summer.*—About 24 days at 16° C.

*Time to develop roots, winter.*—About 28 days at 16° C.

*Root description.*—Fine, fibrous; color, 162C.

*Rooting habit.*—Freely branching; moderately dense.

Plant description:

*General appearance.*—Compact, upright and mounded plant habit; bushy plant form.

*Growth and branching habit.*—Freely basal branching; about ten lateral branches develop per plant. Pinching, that is, removal of the terminal apices, enhances branching with lateral branches potentially forming at every node.

*Plant height.*—about 20 cm.

*Plant diameter or spread.*—About 40 cm.

*Lateral branch description.*—Length: About 20 cm. Diameter: About 2 mm to 3 mm. Internode length: About 2 cm to 2.5 cm. Texture: Pubescent. Color: 144B.

*Foliage description.*—Arrangement: Opposite, simple. Length: About 2 cm. Width: About 1.5 cm. Shape: Lanceolate. Apex: Acute. Base: Obtuse. Margin: Deeply dissected. Texture, upper and lower surfaces: Slightly pubescent. Venation pattern: Pinnate. Color: Developing foliage, upper surface: 146A. Developing foliage, lower surface: 147C. Fully expanded foliage, upper surface: 146A. Fully expanded foliage, lower surface: 147B to 147C. Venation, upper surface: 147A. Venation, lower surface: 147C. Petiole: Length: About 5 mm. Daintier: About 1 mm. Texture, upper and lower surfaces: Smooth. Color, upper surface: 147A. Color, lower surface: 147C.

Flower description:

*Flower type and habit.*—Single upright salverform flowers arranged on hemispherical corymbs. Freely flowering with about 20 to 22 flowers and flower buds per inflorescence. Inflorescences positioned above and beyond the foliage. Flowers last about one week on the plant. Corollas not persistent. Flowers slightly fragrant.

*Flowering season.*—In the garden, flowering is continuous from early spring until fall. Early flowering, plants begin flowering about four to five weeks after pinching.

*Inflorescence height.*—About 4 cm.

*Inflorescence diameter.*—About 3.5 cm to 4 cm.

*Flower size.*—Diameter: About 1.2 cm to 1.3 cm. Height (depth): About 2 cm to 2.2 cm.

*Flower buds.*—Length: About 1 cm to 1.2 cm. Diameter: About 2 mm. Shape: Elongate oblong. Color: N89A.

*Petals.*—Quantity/arrangement: Five per flower fused at base. Length: About 6 mm. Width: About 5 mm. Shape: Roughly cordate. Apex: Emarginate. Margin: Entire. Texture, upper and lower surfaces: Glabrous, smooth; velvety. Color: When opening, upper surface: N87B. When opening, lower surface: N86C. Fully opened, upper surface: N87B; color becoming closer to N88B with development. Fully opened, lower surface: N87D.

*Sepals.*—Quantity/arrangement: Five, fused into an elongated tube. Length: About 1 cm. Diameter: About 1 mm. Shape: Lanceolate. Apex: Acute. Margin: Entire. Texture, upper and lower surfaces: Smooth. Color, immature and mature, inner surface: 147B. Color, immature and mature, outer surface: 147C.

*Peduncles.*—Length: About 3 mm. Diameter: About 1 mm. Strength: Strong. Angle from stem: About 35° to 45°. Texture: Smooth. Color: 137A.

*Reproductive organs.*—Stamens: Quantity: five per flower. Anther shape: Oblong. Anther length: Less than 1 mm. Anther color: 17B. Pollen amount: Scarce. Pollen color: 17B. Pistils: Quantity: One per flower. Pistil length: About 2 mm. Style length: About 1 cm. Style color: 17B. Stigma shape: Bi-parted. Stigma color: 17B. Ovary color: Close to 145A.

*Seeds.*—Length: About 1 mm to 2 mm. Diameter: About 1 mm. Color: 202A.

Disease/pest resistance: Plants of the new *Verbena* have not been observed to be resistant to pathogens and pests common to *Verbena*.

Garden performance: Plants of the new *Verbena* have exhibited good tolerance to rain and wind. In addition, plants of the new *Verbena* have been observed to be tolerant to temperatures ranging from about 0° C. to about 40° C.

It is claimed:

1. A new and distinct cultivar of *Verbena* plant named 'Sumverdi 01', as illustrated and described.

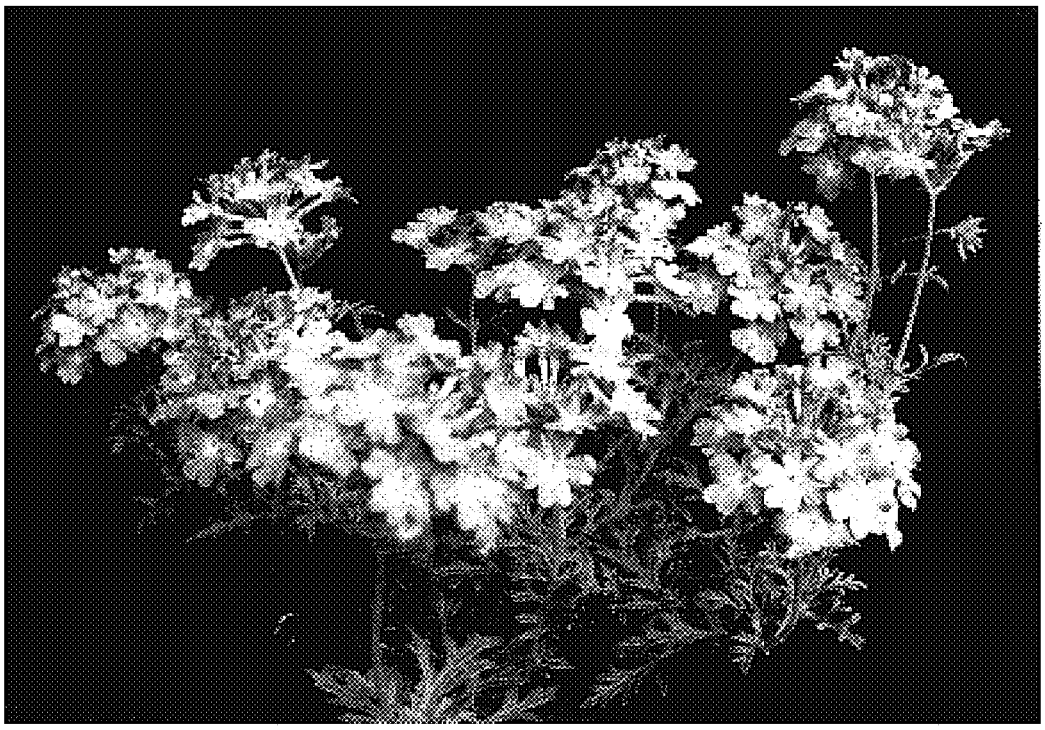

* * * * *